United States Patent [19]
van der Marel et al.

[11] Patent Number: 5,919,461
[45] Date of Patent: Jul. 6, 1999

[54] NONPATHOGENIC INFECTIOUS BURSAL DISEASE VIRUS AND VACCINE

[75] Inventors: Piet van der Marel, Venray; Martinus A. J. Thijssen, Groeningen, both of Netherlands; David Snyder, *deceased, late of* B*owle,* M*d., by* N*ancy* E. S*nyder, personal representative*; Dieter Lütticken, Boxmeer, Netherlands; Ruud Hein, Georgetown, Del.

[73] Assignee: Akzo Nobel N.V., Arnhem, Netherlands

[21] Appl. No.: 08/653,798

[22] Filed: May 28, 1996

Related U.S. Application Data

[63] Continuation-in-part of application No. 08/182,866, Jan. 18, 1994, abandoned, application No. 08/944,525, Sep. 15, 1992, Pat. No. 5,632,989, and application No. 08/423,752, Oct. 18, 1989, abandoned.

[51] Int. Cl.$^6$ .............................. A61K 39/12; C12N 7/04; C12N 7/06; C12N 7/08
[52] U.S. Cl. ..................... 424/204.1; 424/130.1; 424/139.1; 424/141.1; 424/147.1; 424/159.1; 530/388.3; 435/236; 435/237; 435/238; 435/239
[58] Field of Search ................. 424/204.1, 93.2, 424/93.1, 139.1, 140.1, 147.1, 235.1, 236, 331, 159.1; 435/5, 69.3, 173.3, 235.1, 236, 237, 240.21, 238, 239

[56] References Cited

U.S. PATENT DOCUMENTS

| | | | |
|---|---|---|---|
| 4,824,668 | 4/1989 | Melchior et al. | 424/89 |
| 5,192,539 | 3/1993 | Van De Marel et al. | 424/89 |
| 5,518,724 | 5/1996 | Snyder et al. | 424/204.1 |

OTHER PUBLICATIONS

Kibenge et al. "Biochemistry and Immunology of Infectious Bursal Disease Virus". Journal of General Virology. vol. 69:1757–1775, 1988.

Snyder, D.B. et al., "Differentiation of Infectious Bursal Disease Viruses Directly from Infected Tissues with Neutralizing Monoclonal Antibodies: Evidence of a Major Antigenic Shift in Recent Field", Avian Diseases 32, 535–539, 1988.

Mohanty, S.B., Veterinary Virology, Lea & Febiger, Philadelphia, p. 91 (1981).

Rosenberger, J.K. et al., "Isolation & Characterization of Variant Infectious Bursal Disease Virus", Abstract 123 Am. Vet. Med. Assoc. Meeting, p. 357 (1986).

Lütticken, D.R.W. et al.; "Cross Protection Studies in Chickens Involving Different Bursal Disease Subtypes", Amsterdam, pp. 456–459, Sep., 1992.

Rosenberger, J.K. et al., "Update on Delmarva Respiratory Complex and Use of Variant IBDV Vaccines", Proceedings 1986 Poultry Health Condemnation Meeting, Ocean City MD.

Rosenberger, J.K. et al., "Sentinel Bird Survey of Delmarva Broiler Flocks", 1985.

Rosenberger, J.K. et al., "1987 Sentinel Bird Study of Delmarva Poultry", Proceedings Poultry Health and Condemnation Meeting, 1987.

Snyder, D.B. et al., "Rapid Serological Profiling by Enzyme–Linked Immunosorbent Assay", Avian Diseases, vol. 30, No. 1, pp. 139–148 (1985).

*Primary Examiner*—Marian C. Knode
*Assistant Examiner*—Datquan Lee
*Attorney, Agent, or Firm*—William M. Blackstone

[57] ABSTRACT

An Infectious Bursal Disease Virus of the Delaware Variant E type having the characteristics of being able to grow on both VERO cells and CEF cells, reacting with monoclonal antibody BK9 produced by the cell line having ATCC deposit number HB-10157, not causing bursal atrophy after vaccination and not spreading to birds in physical proximity to immunized birds, said virus being identified as Delaware Variant E 89-03.

11 Claims, No Drawings

NONPATHOGENIC INFECTIOUS BURSAL DISEASE VIRUS AND VACCINE

This application is a continuation-in-part of U.S. Ser. No. 08/182,866, filed Jan. 18, 1994, now abandoned; U.S. Ser. No. 07/944,525, filed Sep. 15, 1992, which issued as U.S. Pat. No. 5,632,989; and U.S. Ser. No. 07/423,752, filed Oct. 18, 1989, now abandoned, and full benefit of the filing dates of these applications is claimed. The entire disclosure of each of these applications is included herein by reference. U.S. Ser. No. 07/423,752 is believed to be equivalent to WO 91/05569, published May 2, 1991, which is included herein in its entirety by reference.

DESCRIPTION OF THE INVENTION

We have developed a strain of the Delaware E variant Infectious Bursal Disease Virus that, unlike the original Delaware E Variant, in a live vaccine is not pathogenic in chickens, does not induce bursal atrophy after vaccination, does not spread, and will grow readily in VERO cells and in CEF cells. Live vaccines containing our novel strain protect vaccinated birds against infection by Standard, Delaware and GLS strains. We have designated this unique strain the 89-03 virus.

BACKGROUND OF THE INVENTION

Infectious Bursal Disease, also called "Gumboro Disease," is an acute and highly contagious viral infection of young chickens and other fowl. It is caused by Infectious Bursal Disease Virus (IBDV) Type I. The disease is characterized by degeneration of lymphoid tissue. The primary target of infection is the bursa of Fabricius, although lymphoid damage may also occur in the spleen, thymus, and gland of Harder.

Degeneration of the bursa of Fabricius and other lymphoid tissue in young chickens has severe economic consequences, as the infected chickens have a decreased response to vaccination and an increased susceptibility to other infectious agents.

Immunization is the principal method for controlling the disease. Chickens may be passively immunized, by receiving maternally-derived antibodies, or they may be actively immunized with live (attenuated) or killed (inactivated) vaccines. Live vaccines contain the virus that has been "modified" or attenuated through serial passaging in cell culture. By passaging it is hoped to produce a virus strain that is less pathogenic. In order to be useful in a vaccine, however, it must retain the antigenic and immunogenic properties of the original virus. It must, that is, induce the production of neutralizing antibodies. Control of the disease by immunization had been largely successful until variant strains began to emerge as the result of antigenic drift under field conditions. These variants were causing disease in both actively and passively immunized chickens.

Infectious Bursal Disease Virus is separately classified as Standard, Delaware and GLS. These strains can be characterized using a panel of monoclonal antibodies. The Delaware strain, which is divided into variants A–F, may be the most common IBDV presently found in the United States because existing vaccines have not provided adequate protection against these variants. We have developed a live "variant vaccine" using our novel virus strain 89-03 that will immunize young chickens against the Standard, the Delaware and the GLS variants.

In 1985, Dr. Rosenberger and researchers at the University of Delaware (Rosenberger et al., *Isolation and Characterization of Variant Infectious Bursal Disease Viruses*, Abstr 123rd Am. Vet. Med. Assoc. Meet., p. 357 (1986), isolated variants for which the Standard (ST) type IBD vaccines did not provide satisfactory protection. These variants became known as the Delaware variants. With immunochemical techniques, it was demonstrated by Snyder et al. (Snyder et al. Avian Diseases 32, pp 535–539, (1988) that the Delaware variants were true IBD variant viruses. Using the antigen capture ELISA (AC ELISA) test and monoclonal antibodies R63 and B69, which are directed against different epitopes of Standard IBDV, it was shown that the Delaware variants did not react with B69 monoclonal antibodies and, therefore, had lost their B69 epitope.

In 1989 Dr. Snyder and his coworkers isolated a virulent variant IBDV strain that had lost not only the B69 epitope but also the R63 epitope. This strain is known as GLS.

A large panel of monoclonal antibodies against IBDV Standard and variant strains was prepared by Dr. Snyder at the University of Maryland. Some of the monoclonal antibodies recognize only specific IBDV's. For example, monoclonal antibodies 67 and BK9 are specific for Delaware IBDV variants, whereas 57 is specific for GLS (Table 1).

TABLE 1

Typing IBDV by Antigen Capture ELISA

| Virus Type | Monoclonal Anytibody* | | | | | |
|---|---|---|---|---|---|---|
|  | 8 | R63 | B69 | BK9 | 67 | 57 |
| Standard | + | + | + | − | − | − |
| Delaware Variants | + | + | − | + | + | − |
| GLS Variant | + | − | − | − | − | + |

*All monoclonal antibodies obtained from Dr. David Snyder, University of Maryland, College Park, MD
+ Reacts with monoclonal antibody
− Does not react with monoclonal antibody Using a panel of different monoclonal antibodies, various IBDV types can be recognized. This has been shown to be a useful method to distinguish different IBDV strains.

When antigenic drift occurs and acceptable cross-protection with existing vaccines does not exist, new variant vaccines are required. Inactivated vaccines containing new variants are easier to develop than safe and effective live vaccines, but live vaccines are preferred.

Delaware variant E IBD field virus cannot be used in a live vaccine due to its pathogenicity. It must be attenuated by passaging in eggs or tissue culture to develop a safe live vaccine. Attenuation of Delaware strains in eggs or tissue culture has until the present invention always resulted in the loss of the specific Delaware variant immunological characteristics. Consequently, adapted/attenuated Delaware variant strains have not previously provided satisfactory protection against the homologous field variant strain. This was shown by Dr. Rosenberger, University of Delaware, Newark, Del. and co-workers (supra).

Dr. Rosenberger also showed that adaptation of Delaware variants on eggs or tissue culture decreased the immunogenicity when used in inactivated vaccines. Until now, the only way to prevent loss in antigenicity and/or immunogenicity of the Delaware variants was to grow the virus in the Bursa of Fabricius (Bursae derived antigens). The viral antigens could only be incorporated in inactivated vaccines due to the virulence and pathogenicity of bursal derived virus. To provide adequate protection against Delaware field infections, a live attenuated vaccine must induce the production of specific antibodies that recognize the field-type Delaware IBDV. That means, in the process of attenuation, the immunological characteristics of the Delaware virus must be retained, while pathogenicity and virulence must be reduced or eliminated.

The object of the present invention was to develop a new live vaccine by finding a Delaware E variant IBDV that retained Delaware type antigenicity without the pathogenicity of a field strain.

A further object of this invention was to develop a new and unique IBD virus vaccine strain that permits safe vaccination of all chickens and other fowl against all Standard, Delaware and GLS IBDV variants (Table 2).

TABLE 2

Characterization of Different IBD Viruses by Monoclonal Antibodies

| IBVD Vaccine/Virus | 14 Monoclonal Antibody | | | | |
|---|---|---|---|---|---|
|  | 8 | R63 | B69 | 67 | 57 |
| Classical (USDA/ST)[1] | + | + | + | − | − |
| Delaware Variant E[2] | + | + | − | + | − |
| Delaware Variant A[2] | + | + | − | + | − |
| GLS Variant[3] | + | − | − | − | + |
| 89/03 ™[4] | + | + | − | + | − |
| Primevac IBD-3 ™[4] | + | + | + | + | + |
| Maryland Strain[3] | + | + | + | − | − |
| Clonevac D78 ®[4] | + | + | + | − | − |
| Burcell 1+1 ®[5] | + | + | + | − | − |
| Burcell 2+2 ®[5] | + | + | + | − | − |
| Bursine ®[6] | + | + | + | − | − |
| Bursine 2 ®[6] | + | + | + | − | − |
| Melchior ATCC VR-2161[10] | + | + | + | − | − |
| Sterwin 1084 E[7] | + | + | + | − | − |
| Select S706 ®[5] | + | + | + | − | − |
| Select SVS510 ®[5] | + | + | + | − | − |
| Baxendale PBG-98[4] | + | + | + | − | − |
| Bursavac ®[7] | + | + | + | − | − |
| IBD Blen ®[8] | + | + | + | − | − |
| ASL Variant IBD ®[9] | + | + | + | − | − |

Tests carried out using AC ELISA
+ Reacts with monoclonal antibody
− Does not react with monoclonal antibody
[1]Dr. Rebecca Hyde, USDA, National Veterinary Service Lab, Dayton Road, Ames, Iowa, 50010
[2]Dr. John K. Rosenberger, University of Delaware, 040 Townsend Hall, Newark, Delaware
[3]Dr. Dave Snyder, University of Maryland, AVRWM Guldesky Center, Room 1217, Vet Science Drive, College Park, Maryland 20742
[4]Intervet Inc., 405 State Street, Millsboro, Delaware 19966
[5]Select, P. O. Drawer 2497, Gainsville, Georgia
[6]Solvay (Salsbury Laboratories Inc.) Charles City, Iowa
[7]Sterwin Labs, Rt. 3, Box 537, Millsboro, Delaware 19966. Sterwin 1084 E is Bursa-Vac ® -4.
[8]Sanofi, 7101 College Boulevard, Overland, Park, Kansas 66210
[9]American Scientific Lab, Schering Corporation, Madison, Wisconsin 53707
[10]American Type Culture Collection (ATCC) Rockville, Maryland

SUMMARY OF THE INVENTION

We developed the 89-03 virus by serial passaging the Delaware Variant E in VERO cells. The 89-03 virus is characterized by its ability to grow on both VERO and CEF (chicken embryo fibroblast) cells. It is also characterized by reaction against specific monoclonal antibodies. The 89-03 virus is the only live attenuated Variant E derived virus that still reacts with all of the same monoclonals that react with the original virulent Delaware Variant E, specifically, the BK9 (ATCC deposit number HB-10157) and 67 monoclonals.

The 89-03 live virus vaccine provides at least 90% protection against the Standard, the Delaware and the GLS variant strains of IBD when given by injection, preferably subcutaneously or intramuscularly. The virus, because it is avirulent, does not provide adequate protection when given by oral route of administration. This is the only live variant vaccine characterized by the above monoclonals that does not cause bursal atrophy. In addition, the virus does not spread to other chickens, as evidenced by lack of virus reisolation after vaccination.

DETAILED DESCRIPTION OF PREFERRED EMBODIMENTS

The 89-03 virus has some unique characteristics that distinguish it from other bursal disease viruses and from the Delaware Variant E virus, from which it was derived. It is the first derivative of the Delaware Variant E that is not pathogenic but still retains the same epitopes. Reaction against a panel of monoclonal antibodies showed that 89-03 is the only virus that displays the same reaction pattern as the original Delaware E virus. This indicates that the 89-03 virus retained these original epitopes, while other Variant E derivatives, such as Sterwin 1084E and Melchior ATCC VR 2161, lost some of the characterizing epitopes, i.e., the BK9 and 67 markers. See Table 3.

TABLE 3

Monoclonal Antibody Reaction Patterns
Reaction With Different Monoclonal Antibodies*

| Virus strain | R63 | 8 | B29 | BK9 | 10 | 67 | 57 |
|---|---|---|---|---|---|---|---|
| Classical ST | + | + | + | − | + | − | − |
| D78 | + | + | + | − | + | − | − |
| Delaware E | + | + | + | + | − | + | − |
| 89-03 | + | + | + | + | − | + | − |
| GLS | − | + | + | + | + | − | + |
| 1084 E Sterwin | + | + | + | − | + | − | − |
| Melchior ATCC VR 2161 | + | + | + | − | NT** | − | − |

*ATCC numbers for monoclonal antibodies are: R63 (ATCC 9437), 8 (ATCC 10174), B29 (ATCC 9746), BK9 (ATCC 10157),67 (ATCC 11122), 57 (ATCC 10156), B69 (ATCC 9490), and 179 (ATCC 10158).
**NT means not tested.

Another indication that the 89-03 virus has remained antigenically the same as the original Delaware E Variant is neutralization. Monoclonal 67 was reacted against several bursal viruses, including Sterwin 1084E and Melchior's ATCC VR-2161. Only the 89-03 virus and the original Delaware Variant were neutralized. See Table 4.

TABLE 4

Virus Neutralization Test Results
Different Viruses Using the Delaware Variant
Specific MOAB 67

| Virus | Virus Titer (EID/ML) | Neutralization** Index |
|---|---|---|
| STC | 5.0 | 0 |
| 1084E | 4.6 | 2.9 |
| 89-03 | 3.5 | >3.0* |
| Sterwin 1084E | 5.0 | 0 |
| GLS | 2.7 | 0 |

*Sample was titrated to 3.0 but not beyond
**Method of Mohanty et al., Veterinary Virology, Lea & Febiger, Philadelphia, p 91, (1981)

Although 89-03 is antigenically the same as the original Delaware E Variant, 89-03 has unique and advantageous characteristics that distinguish it from the original.

The 89-03 virus is no longer pathogenic in chickens. The virus does not induce bursal atrophy at any time after vaccination, whereas the original Delaware E Variant caused marked bursal atrophy at nine days post-inoculation. See Table 5.

TABLE 5

Safety Test in One-Day-Old SPF* Chickens

| Vaccine | Days Post Vaccination | No. of Birds with Bursal Atrophy/Total |
|---|---|---|
| Negative Control | 4 | 0/10 |
| Negative Control | 14 | 0/10 |
| 89-03 | 4 | 0/10 |
| Positive Control STC | 4 | 10/10 |
| 89-03 | 14 | 0/25 |
| 89-03 | 21 | 0/25 |
| Delaware E | 9 | 12/12 |

*Specific pathogen free

The 89-03 virus is also different from the original Delaware E Variant in that it will grow readily in VERO cells or in CEF cells. The Delaware E virus can only be propagated in chickens or in embryonated eggs. 89-03 is the only Variant E virus grown in cell culture that provides at least 90% protection against challenge with Standard, Variant E, and GLS variants. See Table 6.

TABLE 6

Immunogenicity Study

| Vaccine | Challenge | Protection |
|---|---|---|
| 89-03 | STC* | 100% |
| 89-03 | Delaware Variant E | 98% |
| 89-03 | GLS | 100% |

*USDA STD Government challenge virus

Differences between 89-03 and the original Delaware E Variant can also be seen in infected chickens. The 89-03 virus does not replicate to a large degree in the bird, and the virus cannot be reisolated. Delaware E virus is easily reisolated in the bursa of Fabricius at four days post-inoculation. Moreover, the 89-03 virus does not spread from bird to bird, as evidenced by lack of protection of birds in close physical proximity to 89-03 inoculated birds. See Table 7. Delaware E, by contrast, is highly contagious. Another indication of the reduced invasiveness of the 89-03 virus is that it must be injected in order for it to provide protection. When given by a natural route, such as intraocularly, the virus only provides marginal protection. See Table 8.

TABLE 7

Contact Spread of 89-03 Protection After Challenge With:

| | | Challenge STC | | Challenge Delaware Variant E | |
|---|---|---|---|---|---|
| Vaccine | Route | R63 ELISA on bursa | HISTO | BBW | HISTO |
| 89 03 | Subcutaneous | 87.5% (7/8) | 100% (8/8) | 90% (9/10) | 90% (9/10) |
| Contact Birds | — | 0% (0/4) | 0% (0/4) | 0% (0/4) | 0% (0/4) |

TABLE 8

Subcutaneous vs. Intraocular Vaccination

| Vaccine | Route | Challenge | Percent of Protection |
|---|---|---|---|
| None | — | STC | 0% |
| 89-03 | Ocular | STC | 60% |
| 89-03 | S.C. | STC | 100% |
| None | — | Delaware Variant E | 0% |
| 89-03 | Ocular | Delaware Variant E | 27% |
| 89-03 | S.C. | Delaware Variant E | 91% |

S.C.—subcutaneous

As the 89-03 virus must be given by injection, it is useful in that it can be mixed with Marek's disease vaccines, Turkey Herpes Virus (HVT), Chicken Herpes Virus (SB-1) and combinations thereof. The 89-03 virus does not interfere significantly with protection provided by either HVT or HVT/SB-1 vaccine. See Tables 9 and 10. Conversely, the Marek's vaccines do not interfere with protection provided by 89-03. See Table 11. IBDV 89-03 can be combined with the other vaccines that are administered by injection, such as with Reo virus vaccines. Preferred combination vaccines include IBDV 89-03 with Marexine™ (HVT), with SB-1, or with both Marexine™ and SB-1.

TABLE 9

Interference Study Results

| | | | Protection[2] | |
|---|---|---|---|---|
| Group | Vaccine | Dose[1] | No. of Chickens | % |
| A | HVT 89-03 | 514 6 Log 10 | 28/50 | 56 |
| B | HVT | 514 | 30/50 | 60 |
| C | None | — | 11/50 | 22 |

[1]HVT dose is in PFU (plaque Forming Units) per bird IBD 89-03 dose is in $TCID_{50}$ per bird
[2]Protection indicates a lack of Marek's disease lesions

TABLE 10

Interference Study Results

| | | | No. Pos./ | Protection | |
|---|---|---|---|---|---|
| Group | Vaccine | Challenge | Total | % | PI |
| A | HVT/SB-1/89-03 | RB1B** | 5/34 | 85 | 84 |
| B | HVT/SB-1* | RB1B | 3/33 | 91 | 90 |
| C | HVT | RB1B | 12/39 | 69 | 66 |
| D | None | RB1B | 33/36 | 8 | — |
| E | None | None | 0/25 | — | — |

*Available from Dr. K. A. Schot, Cornell University
**USDA Marek's Disease Virus (MDV) challenge virus.

TABLE 11

Interference Study Results

| | | | Protection[2] | |
|---|---|---|---|---|
| Group | Vaccine | Challenge[1] | No. of Chickens | % |
| A | HVT SB-1 89-03 | STC[1] | 35/39[2] | 90 |
| B | 89-03 | STC | 31/32 | 97 |
| C | None | STC | 1/29 | 3 |
| D | HVT SB-1 89-03 | E[3] | 41/42[4] | 98 |
| E | 89-03 | E | 39/40 | 98 |
| F | None | E | 0/10 | 0 |

[1]Standard Challenge
[2]Protection determined by gross macroscopic observations described in results section
[3]Delaware Variant Challenge
[4]Protection determined by gross macroscopic observations described in results section and by microscopic examination of suspect bursae outlined in FIG. 3

EXAMPLE I

Two groups of 20 SPF birds were vaccinated with 4.8 log $TCID_{50}$ of Clone Vac D78 by eye drop and, the other group, with 5.2 log $TCID_{50}$ of Variant E 89-03 by subcutaneous injection.

At 21 days of age birds were bled and infected with either the classic challenge virus STC or the Delaware challenge Virus Variant E. Protection was assessed by bursa to body weight ratio seven days p.c. (post challenge) in the case of the variant virus challenge, and by antigen ELISA on bursal tissue three days post challenge in the case of the ST Challenge virus. Results are summarized in Table 12.

The antibody response induced in the homologous system is higher. However, the 89-03 variant virus is able to induce a relatively high response to the standard strain in the heterologous system, which is confirmed by a higher degree of cross protection.

89-03 variant virus can be administered in killed (inactivated) vaccines and in modified live (attenuated) vaccines, alone or in combination with other antigens. The preferred method of administration is by injection, preferably subcutaneously. Vaccines comprising 89-03 variant virus may comprise the pharmaceutically acceptable additives, adjuvants, carriers and diluents that are commonly used in veterinary practice. A vaccine comprising 89-03 variant virus shall contain a sufficient number of virus particles to induce an immune response. This immune response may be enhanced using adjuvants. An effective vaccine may comprise from about $10^{2.5}$ to about $10^9$ virus particles. The product of cell culture production will normally comprise from about $10^3$ to about $10^8$ virus particles. An effective vaccine may be prepared comprising growth medium and cellular material from cell culture without having a negative effect on vaccine performance. Thus, purification of viral material is permissible but not necessary. It is also permissible to concentrate viral material, in which case concentrations in excess of about $10^8$ particles, normally the highest concentration in cell culture, can be achieved. An effective vaccine can be prepared comprising about $10^3$ to about $10^5$ virus particles. A preferred vaccine will comprise about $10^{3.5}$ virus particles.

Infectious bursal disease virus Delaware Variant E 89-03 was deposited Jan. 18, 1994, with the American Type Culture Collection, 12301 Parklawn Drive, Rockville, Md., 20852, USA and assigned accession number VR-2441.

TABLE 12

Serology and Protection Data Three Weeks After Day Old Vaccination of SPF Birds with Live Vaccines

| | [2]log Virus neutralizing Antibody responses | | No. of birds protected/ tested against 100 $CID_{50}$ of | |
|---|---|---|---|---|
| Virus → Vaccine ↓ | Virus Neutralized D78 | Virus Neutralized Var.E/89-03 ™ | STC Challenge Bursa Elisa | Delaware Variant E Challenge Bursa/Body Weight |
| Clone Vac D78 ®* eye drop | 8.7 ± 2.4 | ≦5.2 ± 0.3 | 10/10 | 5/10 |
| Var. E/89-03 ™ s.c. | 7.8 ± 1.6 | 9.5 ± 1.0 | 7/8 | 9/10 |
| Controls | <4 | <4 | 0/10 | 0/6 |

*Standard strain ATTC Deposit No. VR-2041

We claim:

1. An Infectious Bursal Disease Virus Delaware Variant E 89-03, ATCC deposit number VR 2441, and subclones thereof having the characteristics of being able to grow on both Vero cells and CEF cells, reacting with monoclonal antibody BK9 produced by the cell line having ATCC deposit number HB-10157 and with monoclonal antibody 67 produced by the cell line having ATCC deposit number HB-11122, and not causing bursal atrophy after vaccination.

2. A vaccine comprising an immunogenically effective amount of the virus according to claim 1 and pharmaceutically acceptable diluents in a preparation for injection.

3. A method for immunizing birds against Infectious Bursal Disease comprising preparing the vaccine of claim 2 and administering by injection an effective amount of said vaccine for raising protective antibodies to said bird.

4. The vaccine according to claim 2, comprising about $10^{2.5}$ to about $10^9$ virus particles.

5. The vaccine according to claim 2, comprising about $10^3$ to about $10^8$ virus particles.

6. The vaccine according to claim 2, comprising about $10^3$ to about $10^5$ virus particles.

7. The vaccine according to claim 2, further comprising an immunogenically effective amount of Chicken Herpes Virus.

8. The vaccine according to claim 2, further comprising an immunogenically effective amount of Reo Virus.

9. The vaccine according to claim 8, further comprising an immunogenically effective amount of Reo Virus.

10. The vaccine according to claim 8, further comprising an immunogenically effective amount of Chicken Herpes Virus.

11. The vaccine according to claim 10, further comprising an immunogenically effective amount of Reo Virus.

* * * * *